US00PP16608P2

(12) United States Plant Patent
Pieters

(10) Patent No.: US PP16,608 P2
(45) Date of Patent: Jun. 6, 2006

(54) ***CHRYSANTHEMUM* PLANT NAMED 'GOLDEN SURFER'**

(50) Latin Name: *Chrysanthemum×morifolium*
Varietal Denomination: Golden Surfer

(75) Inventor: Luc Remi Johan Pieters, Staden-Oostnieuwkerke (BE)

(73) Assignee: Pieters Joseph & Luc B.V.BA, Staden-Oostnieuwkerke (BE)

( * ) Notice: Subject to any disclaimer, the term of this patent is extended or adjusted under 35 U.S.C. 154(b) by 98 days.

(21) Appl. No.: 11/055,810

(22) Filed: Feb. 11, 2005

(51) Int. Cl.
*A01H 5/00* (2006.01)

(52) U.S. Cl. ..... Plt./295
(58) Field of Classification Search ..... Plt./295
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Golden Surfer', characterized by its upright and rounded growth habit; freely branching growth habit; uniform and freely flowering habit; duplex-type inflorescences with bright yellow-colored ray florets and yellow green-colored disc florets; and excellent garden performance.

1 Drawing Sheet

Botanical designation: *Chrysanthemum×morifolium.*
Cultivar denomination: 'Golden Surfer'.

BACKGROUND OF THE INVENTION

The present invention relates to a new and distinct cultivar of *Chrysanthemum* plant, botanically known as *Chrysanthemum×morifolium* and referred to by the name 'Golden Surfer'.

The new *Chrysanthemum* is the product of a planned breeding program conducted by the Inventor in Staden, Belgium. The objective of the breeding program is to develop new garden *Chrysanthemums* with a flowering date of mid-September, unique inflorescence forms, attractive ray and disc coloration and good resistance to wind and rain.

The new *Chrysanthemum* originated from a cross-pollination made by the Inventor in September, 2000, in Staden, Belgium, of the *Chrysanthemum×morifolium* cultivar Bronia, not patented, as the female, or seed, parent with the *Chrysanthemum×morifolium* cultivar Rumba, disclosed in U.S. Plant Pat. No. 8,462, as the male, or pollen, parent. The new *Chrysanthemum* was discovered and selected by the Inventor as a single plant within the progeny of the stated cross-pollination in a controlled environment in Staden, Belgium.

Asexual reproduction of the new *Chrysanthemum* by terminal cuttings in Staden, Belgium since November, 2001, has shown that the unique features of this new *Chrysanthemum* are stable and reproduced true to type in successive generations.

BRIEF SUMMARY OF THE INVENTION

The cultivar Golden Surfer has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Golden Surfer'. These characteristics in combination distinguish 'Golden Surfer' as a new and distinct cultivar:

1. Upright and rounded growth habit.
2. Freely branching growth habit.
3. Uniform and freely flowering habit.
4. Duplex-type inflorescences with bright yellow-colored ray florets and yellow green-colored disc florets.
5. Excellent garden performance.

Plants of the new *Chrysanthemum* can be compared to plants of the female parent, the cultivar Bronia. In side-by-side comparisons conducted in Staden, Belgium, plants of the new *Chrysanthemum* differed from plants of the cultivar Bronia in the following characteristics:

1. Plants of the new *Chrysanthemum* flowered about 39 days earlier than plants of the cultivar Bronia grown under natural season conditions.
2. Plants of the new *Chrysanthemum* and the cultivar Bronia differed in inflorescence form and ray floret coloration.

Plants of the new *Chrysanthemum* can be compared to plants of the male parent, the cultivar Rumba. In side-by-side comparisons conducted in Staden, Belgium, plants of the new *Chrysanthemum* differed from plants of the cultivar Rumba in the following characteristics:

1. Plants of the new *Chrysanthemum* flowered about 44 days earlier than plants of the cultivar Rumba grown under natural season conditions.
2. Plants of the new *Chrysanthemum* and the cultivar Rumba differed in inflorescence form and ray floret coloration.

Plants of the new *Chrysanthemum* can be compared to plants of the cultivar Pjhavan, disclosed in U.S. Plant Pat. No. 14,268. In side-by-side comparisons conducted in Staden, Belgium, plants of the new *Chrysanthemum* differed from plants of the cultivar Pjhavan in the following characteristics:

1. Plants of the new *Chrysanthemum* were more rounded in form than and not as upright as plants of the cultivar Pjhavan.

2. Plants of the new *Chrysanthemum* flowered about two weeks earlier than plants of the cultivar Pjhavan grown under natural season conditions.
3. Inflorescences of plants of the new *Chrysanthemum* were smaller than inflorescences of plants of the cultivar Pjhavan.
4. Plants of the new *Chrysanthemum* and the cultivar Pjhavan differed in ray floret coloration.

Plants of the new *Chrysanthemum* can also be compared to plants of the cultivar Orka, not patented. In side-by-side comparisons conducted in Staden, Belgium, plants of the new *Chrysanthemum* differed from plants of the cultivar Orka in the following characteristics:

1. Plants of the new *Chrysanthemum* were larger and more rounded in form than plants of the cultivar Orka.
2. Plants of the new *Chrysanthemum* flowered about four days earlier than plants of the cultivar Orka grown under natural season conditions.
3. Plants of the new *Chrysanthemum* and the cultivar Orka differed in inflorescence form and ray floret coloration.
4. Plants of the new *Chrysanthemum* were not sensitive to Rust infection whereas plants of the cultivar Orka were sensitive to Rust infection.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum*.

The photograph at the top of the sheet comprises a side perspective view of a typical flowering plant of 'Golden Surfer'.

The photograph at the bottom of the sheet comprises a close-up view of the upper and lower surfaces of typical leaves (top) and typical inflorescences (bottom) of 'Golden Surfer'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the summer and fall in Oostnieuwkerke-Staden, Belgium, under commercial practice in an outdoor nursery. During the production of the plants, day temperatures averaged 15° C. and night temperatures averaged 13° C. Plants were pinched about two weeks after planting. Plants were about four months from planting into 19-cm containers when the photographs and the description were taken.

Botanical classification: *Chrysanthemum×morifolium* cultivar Golden Surfer.

Commercial classification: Garden Chrysanthemum.

Parentage:

*Female or seed parent.*—*Chrysanthemum×morifolium* cultivar Bronia, not patented.

*Male or pollen parent.*—*Chrysanthemum×morifolium* cultivar Rumba, disclosed in U.S. Plant Pat. No. 8,462.

Propagation:

*Type.*—Terminal tip cuttings.

*Time to initiate roots, summer.*—About 10 days at 25° C.

*Time to initiate roots, winter.*—About 12 days at 20° C.

*Time to produce a rooted cutting, summer.*—About two weeks at 25° C.

*Time to produce a rooted cutting, winter.*—About three weeks at 20° C.

*Root description.*—Fibrous, fine and freely branching; white in color.

Plant description:

*Appearance.*—Herbaceous potted *Chrysanthemum* typically grown as a spray type. Stems upright and outwardly spreading; rounded plant habit. Freely branching with lateral branches potentially developing at every node; dense and full plants. Vigorous growth habit.

*Plant height.*—About 45 cm.

*Plant width.*—About 60 cm.

*Lateral branches.*—Length: About 30 cm. Diameter: About 2 mm. Strength: Strong, flexible. Texture: Pubescent. Color: 146B.

*Foliage description.*—Arrangement: Alternate, simple. Length: About 4 to 5 cm. Width: About 3 to 3.5 cm. Apex: Acuminate. Base: Attenuate. Margin: Palmately lobed. Texture, upper and lower surfaces: Pubescent, leathery. Venation pattern: Pinnate; reticulate. Color: Developing foliage, upper surface: 137C. Developing foliage, lower surface: 138B. Fully expanded foliage, upper surface: 147A; venation, 146B. Fully expanded foliage, lower surface: Closest to 147B; venation, 146B. Petiole length: About 2 to 2.5 cm. Petiole diameter: About 1 mm. Petiole color: 147B.

Inflorescence description:

*Appearance.*—Duplex-type composite inflorescences with ray and disc florets developing acropetally on a receptacle. Inflorescences borne on terminals and lateral branches above foliage. Slightly fragrant. Typically grown as a natural spray-type.

*Flowering response.*—Under natural conditions, plants flower in mid-September in Northern Europe.

*Postproduction longevity.*—Inflorescences maintain good color and substance for about four weeks. Inflorescences persistent.

*Quantity of inflorescences.*—Freely flowering, about eight inflorescences develop per lateral stem; uniform inflorescence development.

*Inflorescence bud.*—Height: About 6 mm. Diameter: About 9 mm. Shape: Ovoid. Color: 146B to 146C.

*Inflorescence size.*—Diameter: About 3.2 cm. Depth (height): About 1.5 cm. Disc diameter: About 5 mm.

*Ray florets.*—Shape: Elliptic. Orientation: Initially upright; with development, roughly perpendicular to the peduncle. Length: About 1.6 cm. Width: About 4 mm. Apex: Rounded. Base: Attenuate; short corolla tube. Margin: Entire. Texture, upper and lower surfaces: Smooth, glabrous; satiny. Number of ray florets per inflorescence: About 130. Color: When opening and fully opened, upper surface: 5C; color becoming closer to 5D with development. When opening and fully opened, lower surface: 5D.

*Disc florets.*—Arrangement: Massed at center of receptacle. Shape: Tubular; falcate. Apex: Five-pointed. Length: About 8 mm. Width: About 1 mm. Number of disc florets per inflorescence: About 55. Color: Apex: 151B. Mid-section: 145C. Base: 144C.

*Peduncles.*—Length: About 2.5 to 5 cm. Diameter: About 1 mm. Angle: Mostly erect. Strength: Flexible. Texture: Smooth; glabrous. Color: 146B.

*Reproductive organs.*—Androecium: Present on disc florets only. Gynoecium: Present on both ray and disc florets.

*Seed/fruit.*—Seed and fruit production has not been observed.

Disease/pest resistance: Plants of the new *Chrysanthemum* were not sensitive to Rust infection. Resistance to pests and other pathogens common to *Chrysanthemums* has not been observed on plants of the new *Chrysanthemum.*

Weather tolerance: Plants of the new *Chrysanthemum* have been observed to be very resistant to wind, rain and temperatures ranging from about −3 to 35° C.

It is claimed:

1. A new and distinct cultivar of *Chrysanthemum* plant named 'Golden Surfer', as illustrated and described.

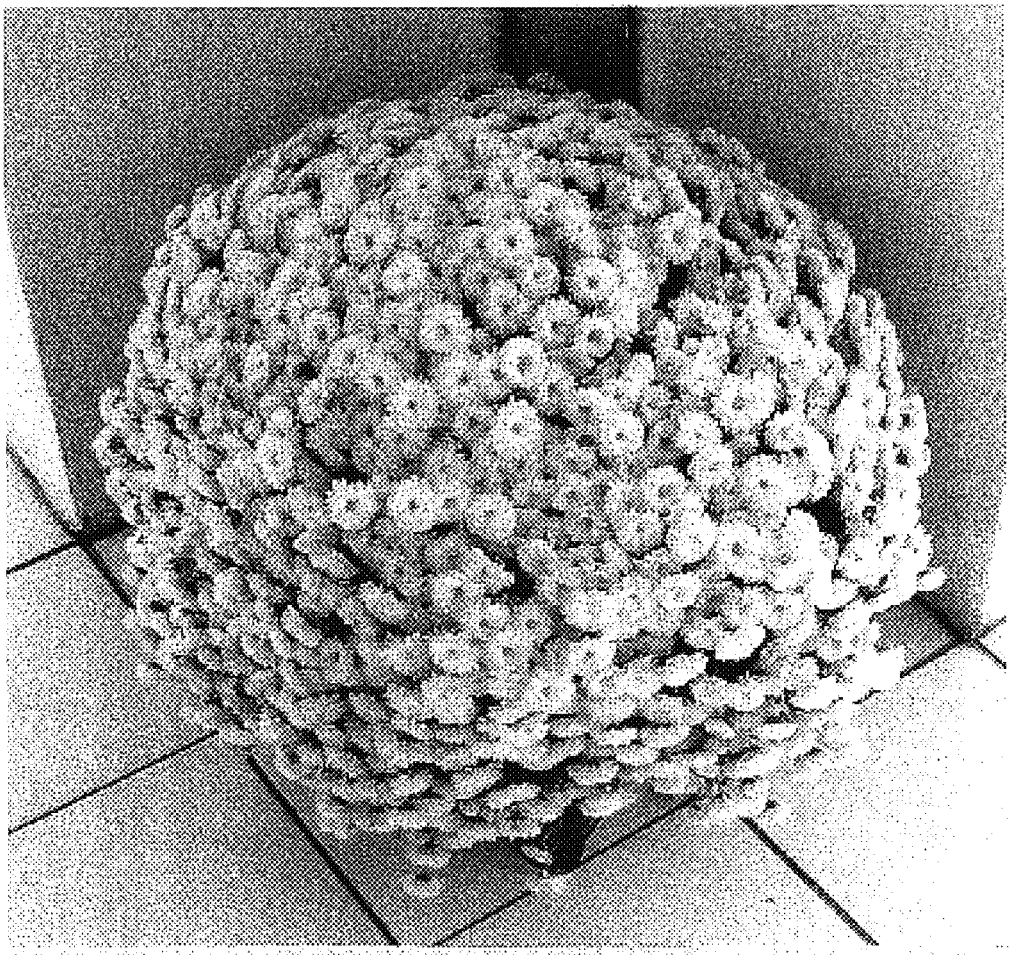
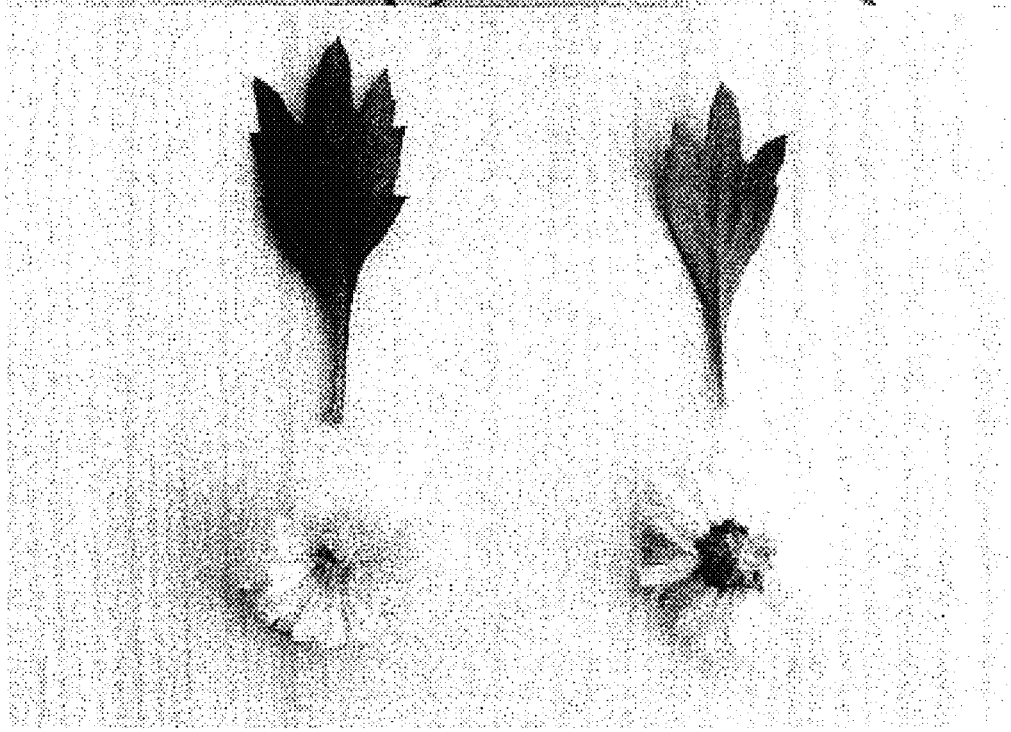

* * * * *